United States Patent [19]

Pedersen et al.

[11] 4,031,111

[45] * June 21, 1977

[54] MACROCYCLIC HETERO IMINE COMPLEXING AGENTS

[75] Inventors: Charles John Pedersen, Salem, N.J.; Marilyn H. Bromels, Wilmington, Del.

[73] Assignee: E. I. Du Pont de Nemours and Company, Wilmington, Del.

[ * ] Notice: The portion of the term of this patent subsequent to Nov. 12, 1991, has been disclaimed.

[22] Filed: Sept. 6, 1974

[21] Appl. No.: 503,777

Related U.S. Application Data

[63] Continuation of Ser. No. 321,575, Jan. 8, 1973, Pat. No. 3,847,949, which is a continuation-in-part of Ser. No. 36,689, May 12, 1970, abandoned.

[52] U.S. Cl. .......................... 260/340.3; 23/230 M; 260/152; 260/239 R; 260/239.3 P; 260/429 CY; 260/429.2; 260/430; 260/431; 260/433; 260/435 R; 260/438.1

[51] Int. Cl.² ............. C07D 273/00; C07D 498/08

[58] Field of Search ..................... 260/239 R, 340.3

[56] References Cited

UNITED STATES PATENTS

| 3,687,978 | 3/1972 | Pedersen | 260/239 R X |
|---|---|---|---|
| 3,847,949 | 11/1974 | Pedersen et al. | 260/239 |

OTHER PUBLICATIONS

Dietrich et al., Tetrahedron Letters, vol. of 1969, No. 34, pp. 2885 to 2888.

*Primary Examiner*—Floyd D. Higel

[57] ABSTRACT

Macrocyclic imines useful as complexing agents for ionic metal compounds characterized by a macrocyclic ring or rings of carbon and hetero-atoms totaling 14–60 ring atoms, at least one hetero-atom being nitrogen and the remainder being oxygen, each hetero-atom in the ring being separated from adjoining hetero-atoms by links of 2 or 3 carbon atoms. The macrocyclic ring or rings are fused to 1–4 carbocyclic rings. The macrocyclic rings or substituted derivatives of them can be monocyclic, bicyclic, or bridged by a carbon, or carbon-hetero-atom chain.

2 Claims, No Drawings

MACROCYCLIC HETERO IMINE COMPLEXING AGENTS

REFERENCES TO RELATED APPLICATIONS

This application is a continuation of application Ser. No. 321,575, filed Jan. 8, 1973 and now U.S. Pat. No. 3,847,949, which in turn is a continuation-in-part of application Ser. No. 36,689, filed May 12, 1970, now abandoned.

This invention relates to macrocyclic ring compounds containing carbon and hetero-atoms, such as nitrogen and oxygen.

Macrocyclic compounds containing 14 to about 28 ring atoms selected from carbon, sulfur, and oxygen atoms are known. They are known to be useful for forming complexing compounds containing certain metal ions whereby reactions with these compounds can take place in media not otherwise useful for this purpose. The complexing ability of macrocyclic compounds is not uniform with all metal ions but is selective and, therefore, not predictable with certainty prior to actual testing. Therefore, solubility, complexing ability, and macrocyclic ring configuration of known macrocyclic complex forming compounds limit their utility.

According to this invention, there are provided certain macrocyclic imines characterized by at least one macrocyclic ring of carbon and hetero-atoms totaling 14–60 ring atoms, at least one hetero-atom being nitrogen and the remainder being oxygen, each hetero-atom in the ring being separated from adjoining hetero-atoms by links of 2 or 3 carbon atoms, and the macrocyclic ring being fused to 1–4 carbocyclic rings from the group: (a) phenylene, naphthalene, phenanthralene, anthralene, and (b) saturated analogs of (a). Substitution derivatives of the above macrocyclic imines are also provided with substituents selected from the group halo, hydro, hydroxy, amino, azo, $C_2$–$C_4$ alkenyl, $C_6$–$C_{12}$ aryl, $C_7$–$C_{16}$ aralkyl, $C_6$–$C_{12}$ cycloalkyl, $C_1$–$C_4$ alkoxy, alkaryl, acyl, cyano, nitro, nitroso, carboxy, sulfo, etc.

Molecular models of the representative compounds of the present invention have configurations suggestive of a crown, lantern, or clam. Accordingly herein, the mono macrocyclic imines are denoted "crown" compounds, the bicyclic macrocyclic imines are denoted "lantern" compounds, and the bridged macrocyclic imines are denoted "clam" compounds. Complexes of these compounds with ionic metals are denoted crown, lantern, or clam complexes. The crown, lantern, and clam compounds of this invention will be referred to herein collectively as crown compounds.

Basically the macrocyclic imines have the structure

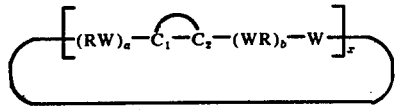

(I)

where W is a hetero atom or group which in this invention is independently an imino group

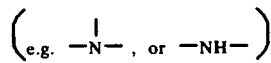

or —NH—) or an oxygen atom with at least one nitrogen atom being present in the macrocyclic ring; R is an alkylene group, i.e. —$CH_2$—$CH_2$— or —$CH_2$—$CH_2$—$CH_2$—; $x$ is an integer of at least 1; $a$ and $b$ are independently 0 or a positive integer; —$C_1$—$C_2$— is a carbocyclic ring such as phenylene, naphthalene, phenanthralene, anthralene, etc., or saturated analogs thereof, such as cyclohexylene, etc.; and $C_1$ and $C_2$ are vicinal carbon atoms in the carbocyclic ring (herein called a fused carbocyclic ring). In other words, the crown compounds of this invention contain a macrocyclic ring fused to 1–4 other aromatic or alicyclic rings (fused rings). The fused rings can be the same or different and can be arylene (e.g. phenylene) or perhydro (fully saturated) analogs thereof (e.g. cyclohexylene) or substituted derivatives of these, the substituents being one or more or a combination of the groups: halo, nitro, amino, azo, alkyl, aryl, aralkyl, acyl, alkoxy, cyano, hydroxy, carboxy, chlorocarbonyl, carbalkoxy, and sulfo, or any other substituents available through the known reactions of organic chemistry. Such groups provide a crown compound with additional functionality and the attendant reactivity and usefulness without detracting from its utility as a complexing agent.

At least two methods are available for synthesizing these substituted crown compounds in which one or more substitutents are attached to one or more fused rings. In one method the substituents are present on an aromatic or alicyclic compound which will serve as the starting point for making a crown. In this case, these substituent groups must, in general, be reasonably stable toward the reactants needed to promote the desired ring-closure reaction. In other words, it should be recognized that substituent groups can be reactive and require appropriate protection during the synthesis according to well-known chemical principles. Standard methods for protecting these reactive groups are well known to those skilled in the art and numerous examples are illustrated herein. Another method involves addition of the substituent group after the crown compound is formed. Typical methods of synthesizing similar substituted crown compounds are described in French Pat. No. 1,440,716 and British Pat. No. 1,149,229 both to Charles John Pedersen.

In accordance with Formula I, the crown compounds are assemblages of three characteristic structural units; i.e., hetero atoms, alkylene groups, and bivalent carbocyclic rings. The hetero atoms are divalent oxygen (—O—) and trivalent nitrogen

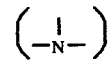

denoted by W in Formula I. The bivalent alkylene groups are 1,2-dimethylene (i.e. ethylene) and 1,3-trimethylene, which are denoted by R in Formula I. Bivalent carbocyclic ring residues or radicals are denoted by —$C_1$—$C_2$— in Formula I.

The alkylene groups, imino groups, and rings can be substituted with groups which do not adversely affect stability of the crown compound. Suitable substituents are determined on the basis of the chemical nature of the unit at the point of attachment, the chemical nature of the crown compound and the chemical procedure used to prepare the crown compound. For instance, because oxygen is divalent, no substituents on an oxygen atom in the macrocyclic ring are possible; both valencies being utilized in forming the ring. Likewise, with two valencies of nitrogen utilized in forming a macrocyclic ring, the third valence can be occupied by hydrogen or by substituents known in the art to be suitable for replacement of hydrogen on a secondary amine.

Included among suitable substituents on nitrogen are such groups as alkyl groups, aryl groups, alkaryl groups, acyl groups, nitroso groups, etc. Examples of these groups include: for alkyl; methyl, ethyl, n-propyl, isopropyl, alkoxyalkyl, and so forth up to about the various isomers of dodecyl; for aryl (including those carrying substituents), phenyl, tolyl, butyl phenyl, naphthyl, chlorophenyl, nitrophenyl, carboxy phenyl, etc.; for alkaryl, benzyl, phenyl ethyl, naphthyl butyl, chlorobenzyl, etc.; for acyl groups (including in broad scope the residues obtained by removing halogen from an acyl halide)

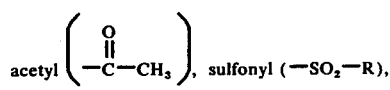

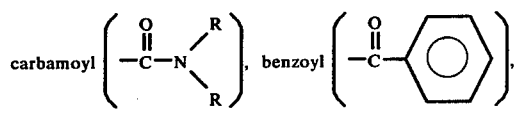

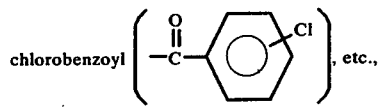

where R is an alkyl, aryl etc.; and the nitroso group ($-N=O$).

Suitable substituents for the alkylene groups include alkyl, aryl, alkaryl and aralkyl groups, such as those illustrated above. As recognized in the art, condensation reactions, which are used to construct the macrocyclic ring system, proceed less satisfactorily when secondary or tertiary derivatives of the alkylene group precursors (e.g. tosyl or chloro) are used. Side reactions intervene and yields are reduced. For this reason it is preferred that a bivalent alkylene group carry only one substituent and not more than one substituent per carbon atom other than hydrogen.

Suitable substituents for the rings include halo, nitro, nitroso, amino, azo, $C_1$-$C_4$ alkyl, $C_1$-$C_4$ alkenyl, $C_6$-$C_{12}$ aryl, $C_7$-$C_{16}$ aralkyl, $C_6$-$C_{12}$ cycloalkyl, $C_1$-$C_4$ alkoxy, cyano, hydroxy, carboxy, sulfo, etc.

Additionally substituents can be a chain of carbon and hetero atoms as in the case where a nitrogen atom or atoms in a ring are attached to another chain of carbon and hetero atoms such as a chain defined by the bracketed portion of Formula I. When this chain of carbon and hetero atoms is joined at the separate ends to two nitrogen atoms in the one macrocyclic ring, a bicyclic ring or lantern compound is formed. When this chain of carbon and hetero atoms is connected at the separate ends of the chain to two nitrogen atoms in different macrocyclic rings, a bridged or clam compound is formed. These compounds are illustrated by the following formulae:

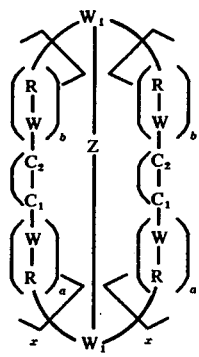

(II)

where R, W, $a$, $b$, $x$ and $-C_1-C_2-$ are defined as above and Z is a bifunctional organic radical, such as alkylene, a chain of carbon and hetero atoms as defined by the bracketed portion of Formula I, or a (WR) group as defined above;

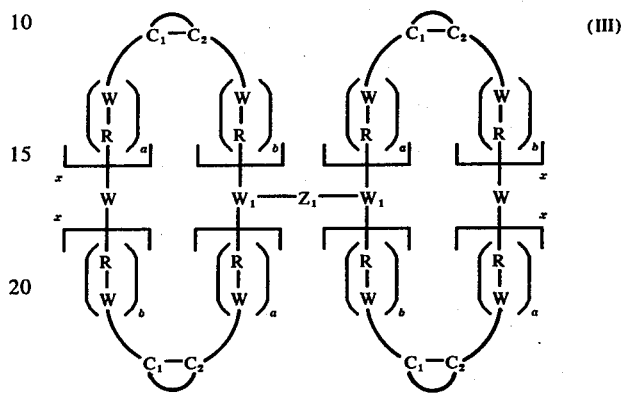

(III)

wherein R, W, $-C_1-C_2-$, $a$, $b$ and $x$ are defined as above; $W_1$ is trivalent nitrogen; $Z_1$ is a bridge consisting of a bifunctional organic radical defined as Z above or a polymeric chain. $-WRW-$ in these formulae are aliphatic groups diterminated with hetero atoms, e.g. $-NH-R-NH-$, $-NH-R-O-$,

etc., where R is $-(CH_2)_2-$, $-(CH_2)_3-$, $-(CH_2)_2-NH-(CH_2)_2-$, $-(CH_2)_2-NH-(CH_2)_2-O-(CH_2)_2-$

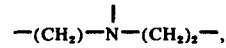

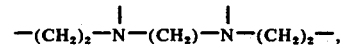

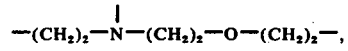

and higher members of these series including the corresponding aliphatic groups in which one or more of the $-(CH_2)_2-$ groups is replaced by $-(CH_2)_3-$.

The term "ring atom" refers to an atom in the chain, e.g. $+(RW)_a - C_1-C_2 - (WR) - W+_x$, of a macrocyclic ring unless specifically used with reference to another ring, such as a carbocyclic ring.

Representative structures of the compounds of this invention are as follows:

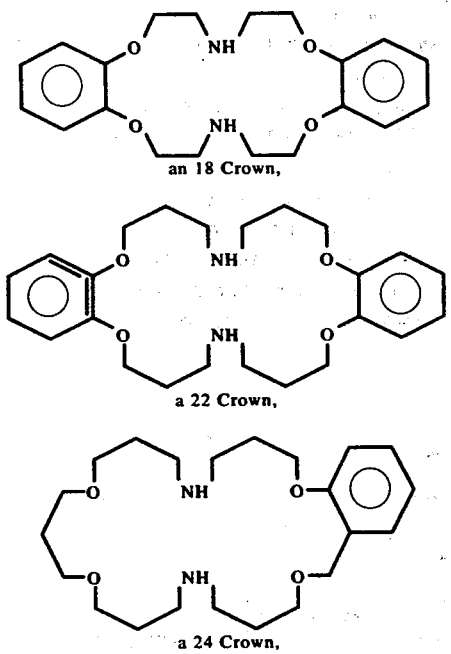

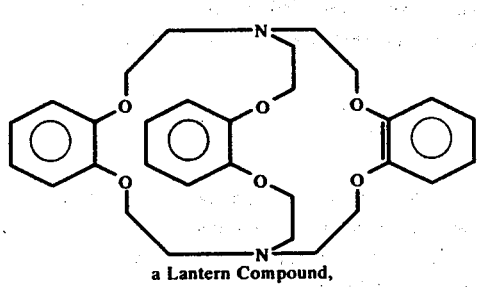

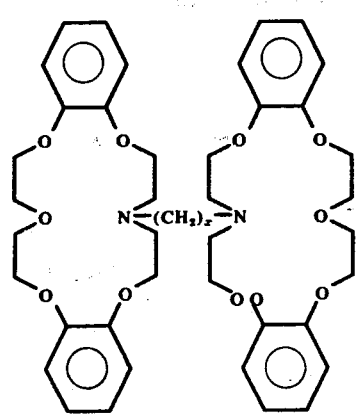

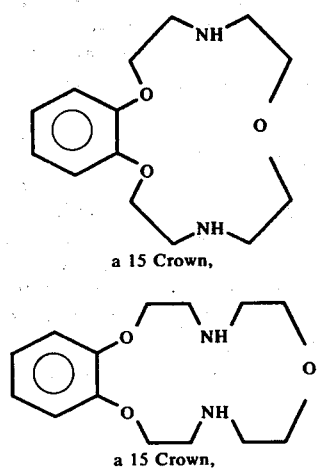

The symbol

refers to an ethylene group $-(CH_2-CH_2)-$,

refers to a trimethylene group $-(CH_2CH_2CH_2)-$, and

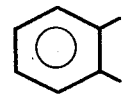

refers to o-phenylene. The notation

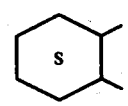

refers to o-cyclohexylene. The above compounds IV, V, VII, and XI contain 18, 22, 24, 14 and 15 carbon and hetero-atoms in the macrocyclic rings are referred to herein as 18 Crown, 22 Crown, 24 Crown, 14 Crown, and 15 Crown, respectively, based on the number of atoms in the macrocyclic rings. Compound IX contains 22 atoms in bicyclic rings and is referred to as a Lantern compound and compound X contains 36 atoms in two macrocyclic rings connected by a polymethylene bridge and is referred to as a Clam compound. Numerous variations of these configurations will be apparent to those skilled in the art from these examples. Macrocyclic Crown, Lantern, and Clam compounds of this invention can be prepared with varying number and sequence of carbon, heteroatoms, and carbocyclic rings.

To promote complexing, hetero atoms in the macrocyclic rings should be separated by links of no more than 3 ring-carbon atoms or no less than 2-ring carbon atoms. Optimally, the ring hetero atoms are separated from adjoining ring hetero atoms by 2 ring carbon atoms, e.g., —CH₂CH₂—. Macrocyclic imines having from 14–30 ring atoms will contain from 4 to 10 hetero atoms, at least one hetero atom being nitrogen. Crowns can be made in which all hetero atoms are nitrogen, but for general utility as complexing agents and with cost of preparation as a consideration a preferred group of imine crowns are those with at least two nitrogens and at least two oxygen atoms in the macrocyclic ring.

Carbocyclic nuclei or rings which are vicinally fused to a macrocyclic ring in the imine crowns, hereinafter sometimes referred to as A, are selected from the group consisting of monocyclic and polycyclic aromatic hydrocarbons of the benzo series consisting of from 1 to 3 fused rings (benzene, naphthalene, anthracene, phenanthrene), and the perhydro analogues thereof. The nuclei can be represented as R-substituted, i.e.

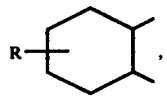

where R is hydrogen, halo, nitro, nitroso, amino, azo, $C_1$–$C_4$ alkyl, $C_2$–$C_4$ alkenyl, $C_6$–$C_{12}$ aryl, $C_7$–$C_{16}$ aralkyl, $C_1$–$C_4$ alkoxy, cyano, hydroxy, carboxy, sulfo and the like and can be attached to any of the four available ring positions. Provided the substituent group is stable with the reactants employed in forming the novel imine crowns of the invention, the group can be present in the vicinally difunctional compounds which are preferred starting materials for the formation of the crown compounds. In other instances the substituent can be introduced after formation of the macrocyclic ring by conventional chemical reaction, e.g., by azo coupling of an amino compound to introduce the azo grouping. In yet other instances, the substituents can be formed by chemical reaction of other substituents, e.g., nitro groups can be reduced to anino groups.

Generally, macrocyclic ring compounds can be made by a series of consecutive and alternative condensation reactions. The particular sequence of reactions is patterned to produce the compound of the desired size and configuration. Numerous examples of these reactions and particular sequences are given herein.

A general synthesis procedure for the nitrogen crowns consists of a series of stepwise condensation wherein aliphatic (or cycloaliphatic) tosylates or aliphatic halides react with amines (having one available H-atom) or phenols or, less preferably, with alcohols. If desired, thiophenols or mercaptans may also be employed. The arrangement of hetero atoms in the crown to be made will determine the sequence of condensation reactions chosen. Representative sequences are illustrated herein. In all cases, undesired side reactions are minimized by employing protective groups to inactivate sites which can compete with the desired ones; with reactants having N-atoms, beta to halo, or tosyl, e.g.

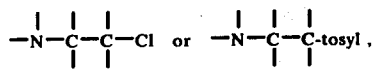

are preferably avoided. Representative protecting groups for amino and hydroxyl are benzyl, tetrahydropyranyl, methoxymethyl, trityl, and tert-butyl carbobenzoxy. References giving other protecting groups are given herein, infra.

The condensations are run in inert solvents, preferably boiling in the range 100°–160° C. Aromatic hydrocarbons, e.g. xylene, glymes, and alcohols are representative classes. The choice of reactants may bear upon the choice of solvents; thus, alcohols are not used as solvents and reactants at the same time.

Imino crowns in which a nitrogen is next to a carbocyclic ring are synthesized from o-amino phenol, o-phenylene diamine or their saturated analogues using one of the following condensations as the primary step:

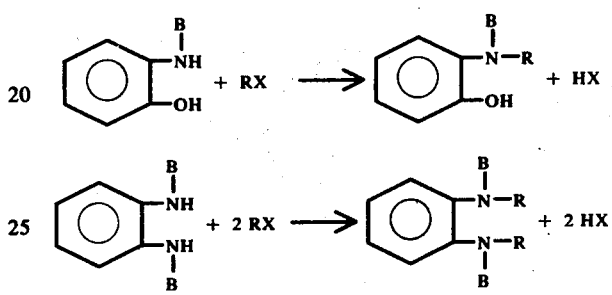

wherein B is a protective group and RX is an alkyl halide or tosylate. RX can be a compound which would form a crown in one step, such as

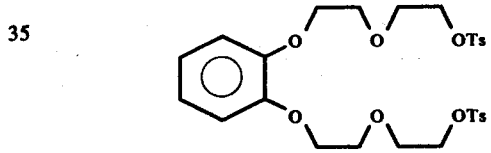

where Ts is tosylate group;
or it can be a compound which would add a short aliphatic chain to the incipient crown, such as

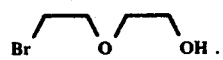

Imino crowns in which a nitrogen is present in a position other than next to a carbocyclic ring can be synthesized from intermediates such as those shown below or other suitably protected compounds:

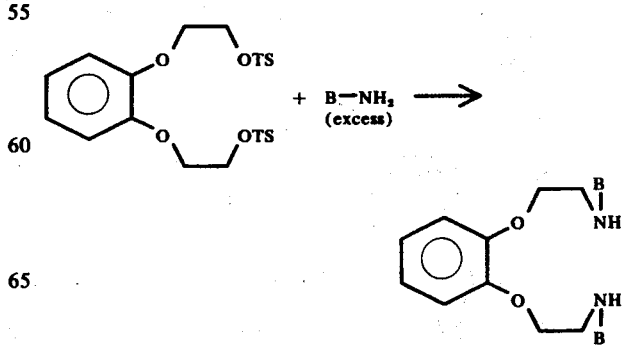

-continued

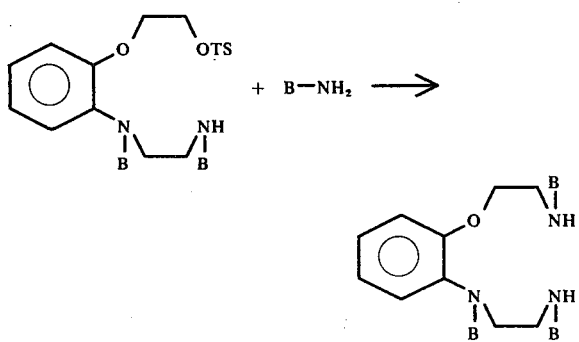

where B is defined as above. The same general conditions as described above apply. Those skilled in the art will be able to devise schemes for syntheses of a variety of imino crowns by judicious protection of hydroxyl and amino groups coupled with stepwise condensations.

Crown compounds containing at least one carbocyclic fused nucleus or ring (e.g. benzo group) can be built up from reactants having a benzenoid nucleus on which hydroxy or amino groups are independently, vicinally positioned (e.g. catechol, o-aminophenol, 1,2-phenylenediamine). If a crown having a single carbocyclic fused nucleus is desired, a bridging group is built up from one of the vicinal groups and joined to the other vicinal group, or a complete bridging group is attached first to one vicinal group and then to the other. If a crown having to carbocyclic fused nuclei is desired, there are several general methods. In one procedure, a bridging group is attached to (or built up from) one vicinal group on a benzenoid nucleus; then two of these compounds are codimerized, each compound supplying one bridging group which joins the free vicinal group of the other to form the macrocyclic ring. In an alternative procedure, a pair of benzenoid nuclei are bridged; then the ends of a bridging group are attached to the free vicinal groups (one on each nucleus) to form the macrocyclic ring. If a crown having more than two carbocyclic fused nuclei is desired, the needed benzenoid nuclei are bridged in a linear manner to give a polymer having terminal benzenoid nuclei bearing one free vicinal group apiece; a bridging group is then attached to these free vicinal groups to form the macrocyclic ring.

Illustrative details will be given below and it will be evident to those skilled in the art that the number and position of the ring nitrogen atoms will influence the selection of a procedure for a specific compound. It will be further evident that classical organic chemical procedures may have to be employed on occasion to protect one or more functional groups present, e.g. one of a pair of vicinal amino or one of a pair of vicinal hydroxyl groups. Procedures for protecting functional groups are well summarized in *Advances in Organic Chemistry*, Vol. III, Interscience Publishers, New York, 1963, pages 159–294.

At one or more stages in the synthesis of the macrocyclic imines of the present invention a chain-lengthening reaction may be required. The reaction of ethylene oxide with a compound (R') containing a hydroxyl or >NH group will add $-(CH_2-CH_2-O)_n-H$ where $n = 1,2,...$. The analogous reaction of oxacyclobutane will add $-(CH_2-CH_2-CH_2-O)_n-H$. Nitrogen atoms can be introduced by converting a hydroxyl group to the tosylate (Ts),

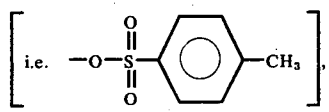

displacing the latter with a benzylamino group ($\Phi-CH_2-NH_2$), and cleaving the benzyl group by hydrogenating (H$_2$) with palladium on carbon catalyst (Pd/C) at 70° C. and 300 psig, e.g.

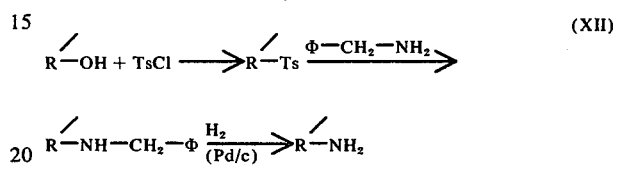     (XII)

Before cleavage the benzylamino-terminated intermediate can be further reacted with Cl—CH$_2$—CH$_2$-OH,

or Br—CH$_2$—CH$_2$—OH e.g. 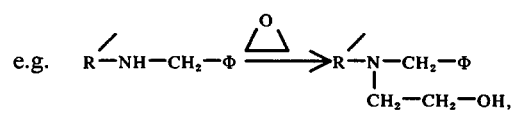

to add —CH$_2$—CH$_2$—OH and one of the above reactions can be repeated. The terminal hydroxyl group can be converted to its tosylate to allow introduction of a second benzylamine group; thus, chains of $-(NH-CH_2-CH_2)_n$ groups can be added. Alternatively, the terminal hydroxyl group can be reacted with an oxide as in the first reaction above to give a link such as —CH$_2$—CH$_2$—O—. If 3-chloropropanol is used in place of ethylene chlorohydrin, $-(NH-CH_2-CH_2-CH_2)_n$ groups result from the tosylate/benzylamine sequence. The spacing between heteroatoms can thus be arranged by selecting the proper ether and the proper alcohol each time the chain is lengthened.

To obtain a fused carbocyclic ring joined to two nitrogen atoms, e.g. —N—C$_1$=C$_2$—N—, a crown compound can be prepared from a 1,2-diamine, e.g., 1,2-phenylenediamine. It is convenient to block (protect) one of the amino groups by reacting it with carbo-t-butyloxy chloride, such as

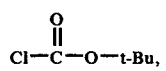

widely used in peptide synthesis, to get the following intermediate:

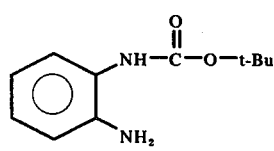

The carbo-t-butyloxy group is removed when desired by 2N HBr in anhydrous acetic acid at 20° C in 30 minutes. When one amino group is free and one is blocked, the free amino group can be used for building the desired bridge; thus

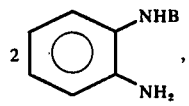

where B = carbo-t-butyloxy, can react with ditosylate of N-benzyldiethanolamine,

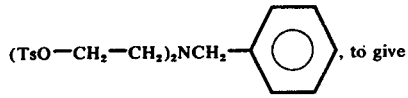, to give

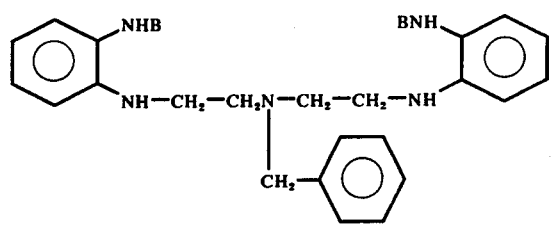

When the carbo-t-butyloxy groups have been selectively removed as described above, the liberated ring —NH₂ groups are ready for reaction with another molecule of the same ditosylate to form

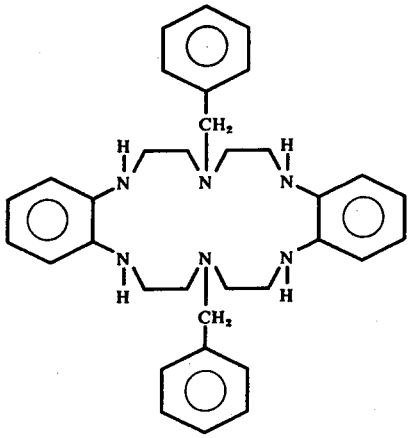

The benzyl groups can be removed by hydrogenating as indicated above.

In another variation,

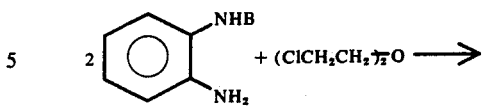

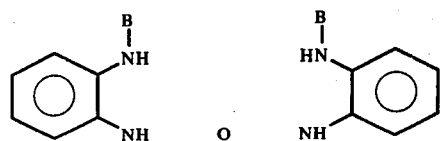

+

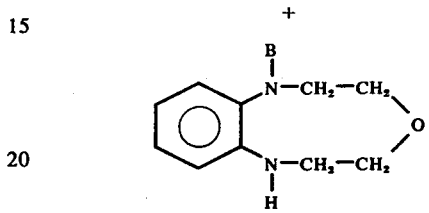

Subsequently liberated amine groups can be reacted with a different Cl-CH₂CH₂O- terminated bridging compound such as

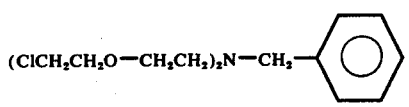

to complete the ring, e.g.

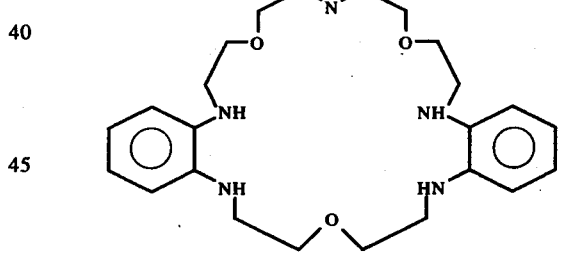

A benzenoid ring can be used having one amino group and one inactive N group which needs no protection. The following sequences illustrate how o-nitro-N-methylaniline is employed:

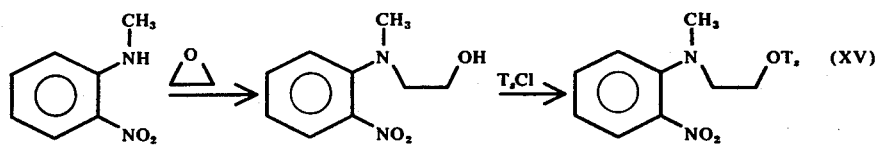

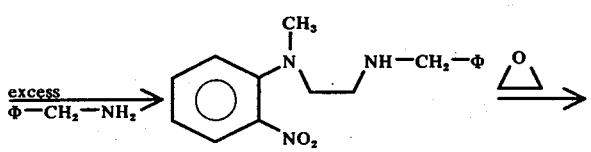

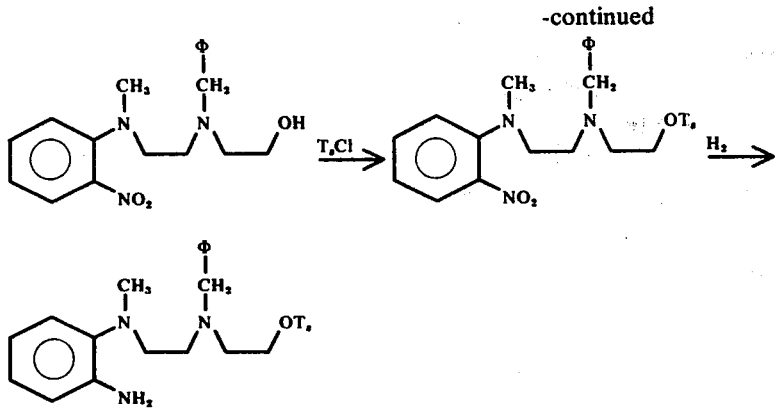

This intermediate is codimerized (in solution using xylene solvent with tert.-amine to neutralize sulfonic acid byproduct and heating to reflux) to yield:

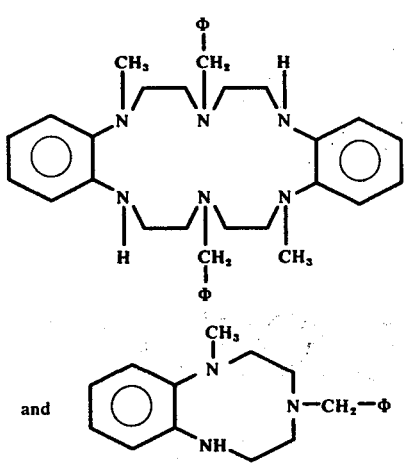

The benzyl groups can be cleaved if desired to give —NH and the desired crown is recovered from by-product by well-known methods.

To obtain a carbocyclic fused ring attached to both N and O, e.g. —O—$\widehat{C_1-C_2}$—N—, o-aminophenol is a preferred starting compound. During the reaction the appropriate groups should be blocked. Reaction of o-aminophenol with a bridging compound such as bis($\beta$-chloroethyl) ether), Cl—CH$_2$CH$_2$—O—CH$_2$CH$_2$Cl, gives an intermediate, e.g.

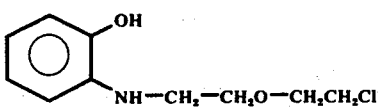

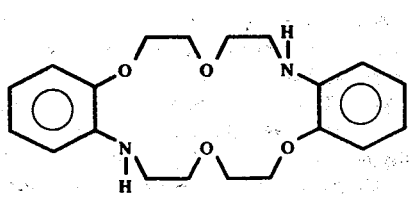

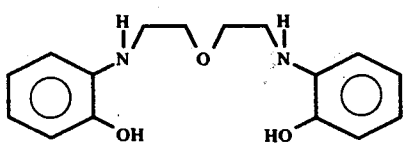

In place of co-dimerization, the intermediate can be reacted with more o-aminophenol to give the bridged bisphenol

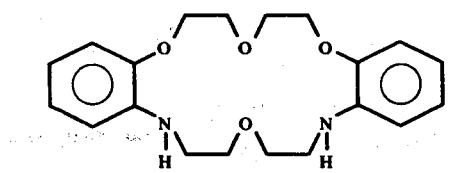

The remaining bridge is completed by reaction with bis($\beta$-chloroethyl) ether in the presence of base to yield:

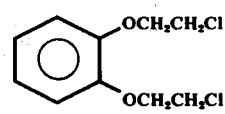

It is evident that a great variety of ethereal dichlorides can be substitued for bis($\beta$-chloroethyl)ether, e.g.

To obtain a carbocyclic fused ring attached only to oxygen, e.g. —O—$\widehat{C_1-C_2}$—O—, catechol is a preferred starting compound. The hydroxyl groups can simultaneously take part in bridge building steps by the general methods stated above. For example, (XVI)

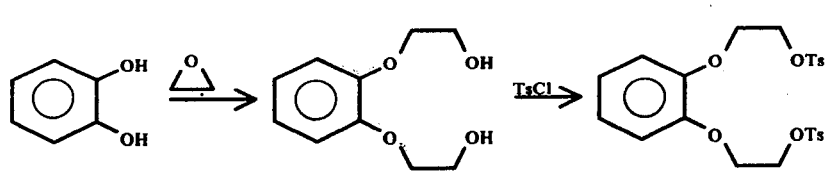

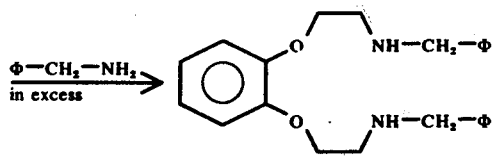

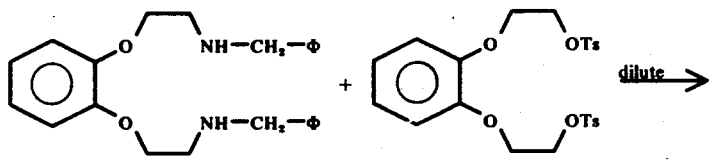

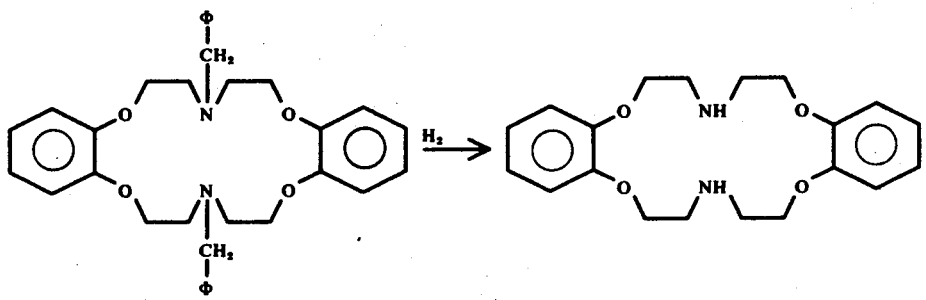

(XVII)

The first three steps of this reaction XVI can be repeated to add additional

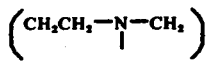

groups, e.g.

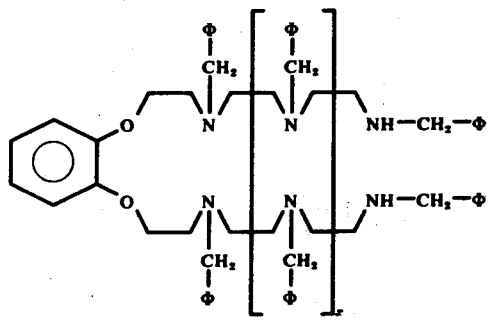

If

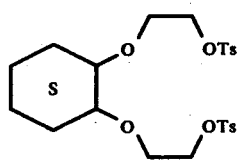

derived from 1,2-cyclohexylene glycol, is substituted in the cyclization step of reaction XVII, one of the fused carbocyclic rings will be saturated,

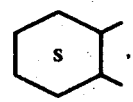

the other will be aromatic

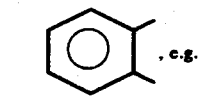, e.g.

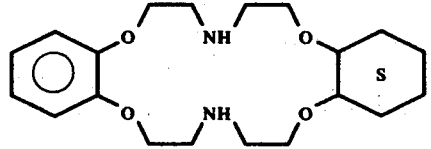

The reactants are maintained at a low concentration (about 0.02 M or less) for the cyclization step to avoid polymerization of the reactants.

A one-step cyclization can occur when cyclohexane ditosylate is reacted with a glycol having a blocked amino group in the presence of a potassium salt (e.g. potassium tert.-butylate) followed by treatment with dilute acid to remove trityl, e.g.

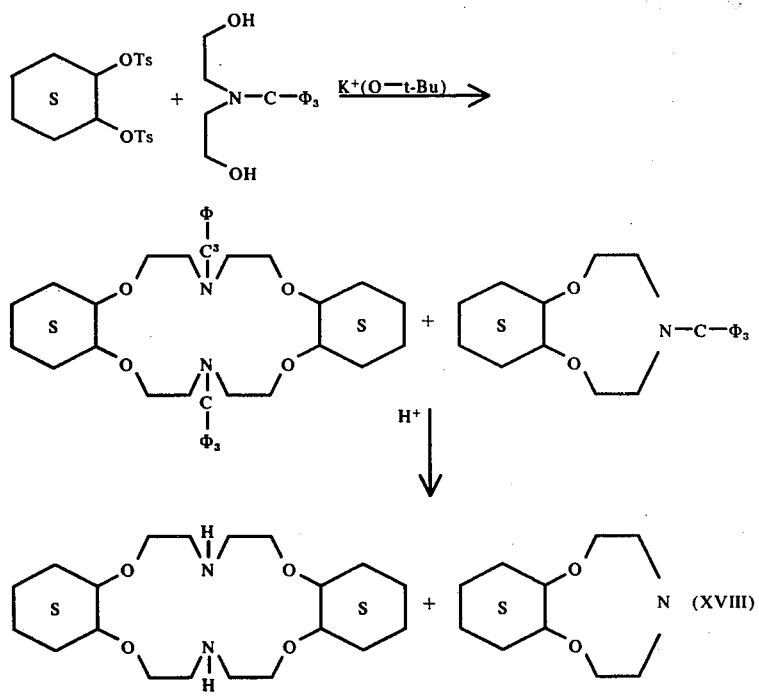

A molar portion of the glycol and a 2-molar portion of base are separately and simultaneously added to a molar portion of the ditosylate in tetrahydrofuran (THF). After the reaction, the desired crown compound is recovered from byproducts by known methods.

To attach one or more ethyleneoxy groups to a benzenoid nucleus having vicinal hydroxyl groups, e.g.

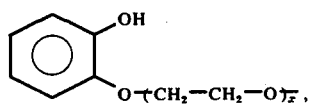

a vicinal dihydroxy aromatic compound is reacted with an aliphatic primary halide having at least one terminal $Cl-CH_2-CH_2-O-$ group in the presence of at least one equivalent of a strong base, preferably sodium hydroxide, for each phenolic hydroxyl group. When necessary, a hydroxyl group can be blocked prior to the above reaction with a carbobenzyloxy group to get the following intermediate:

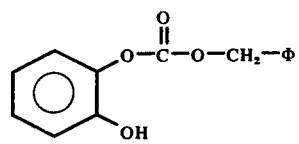

The carbobenzyloxy group is removed when desired by catalytic hydrogenation (Pd/C). Dihydropyran, benzyl, or alphachloromethyl methyl ether (in the presence of strong base) are alternative blocking agents; the phenolic hydroxyl group is regenerated by treatment with acid or by hydrogenation in the case of benzyl.

1,2-Dihydroxylbenzene, such as catechol, can also be reacted with β-haloether groups in the presence of base to attach a bridging element, e.g.

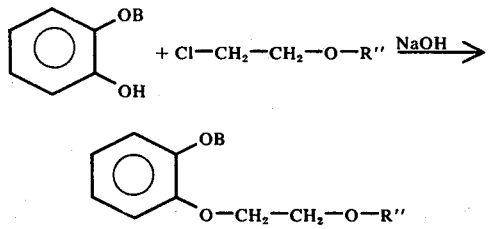

This process is described and illustrated in the aforementioned patents to Charles John Pedersen, i.e. French Pat. No. 1,440,716 and British Pat. No. 1,149,229. It is on the other hand, not desirable to use β-haloamino compounds, i.e., where the halogen atom is separated from a nitrogen atom by two carbon atoms.

Macrocyclic imines having saturated fused carbocyclic groups can be made by hydrogenating the corresponding macrocyles having fused benzenoid groups. As indicated above, they can also be made by bridging vicinally disubstituted saturated carbocyclic compounds, e.g., 1,2-cyclohexylene glycol or 1,2-cyclohexylene-diamine, using cyclic ethers, tosyl chloride, and benzylamine by the methods illustrated above for their aromatic counterparts.

Due to the trifunctionality of nitrogen the crown compounds of this invention can contain macrocyclic rings fused via a pair of N-atoms in a bicyclic structure (e.g. compound IX). The bicyclic structure can be considered two nitrogen atoms connected by three chains of carbon and hetero-atoms. These bicyclic compounds are termed Lantern compounds. The present invention includes bicyclic crowns where at least one fused carbocyclic substituent is present. Each heterocyclic ring preferably has at least 18 atoms. These compounds can have ring N-atoms other than the pair common to the fused heterocyclic rings; ring oxygen atoms can also be present. Adjacent hetero atoms in the rings are separated by 2 or 3 carbon atoms. Obviously each of the heterocyclic rings can have the same sequence and number of atoms or each can be different in either or both respects.

When only two N-atoms are present, the lantern compound can be made by reacting a diimino crown with n-butyl lithium and then reacting the resulting dilithio salt with a diprimary dihalide or ditosylate. Lantern compounds containing fused aromatic carboxylic rings can be prepared by reacting a crown compound having aromatic carboxylic rings and two —NH— groups in approximately opposed positions in the macrocyclic ring with a ditosylate having a fused aromatic carboxylic ring in the presence of BuLi, e.g.,

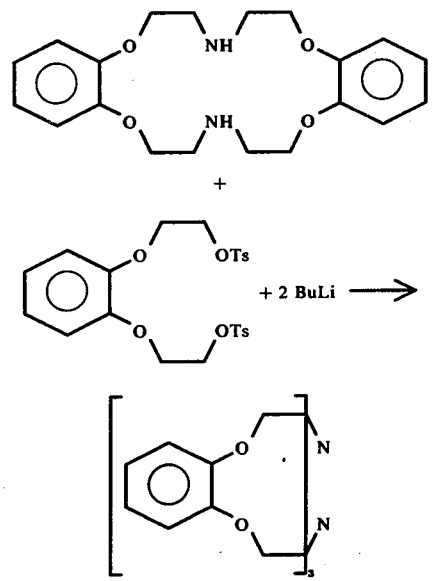

A representative reaction sequence is given in Example 6, infra. Alternatively, an acylation reaction can be used, e.g.

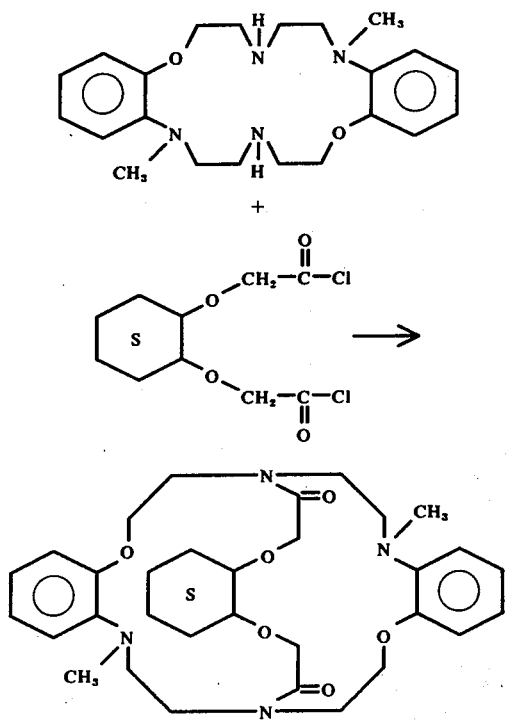

The reaction is conducted at high dilution and reduction of the acyl groups completes the synthesis.

Crown compounds having one unsubstituted ring N-atom can be bridged by a divalent group containing alkylene groups and hetero atoms to form clam compounds (e.g. see compound X, supra). The n-butyl lithium reaction can be used to produce the clam compound. This process consists essentially of reacting an imino crown compound with n-butyl lithium to produce a dilithio salt, then reacting the dilithio salt with a compound selected from the group of diprimary dihalide and ditosylate to produce a clam compound, and recovering the clam compound. This novel process is a general procedure for alkylating an imine group which cannot be alkylated by previously known methods. The general process consists essentially of reacting the imine with n-butyl lithium to produce a lithio salt, then reacting the lithio salt with a compound selected from the group of primary alkyl halide and primary alkyl tosylate to produce the alkylated imine, and recovering the alkylated imine.

Other ring N atoms can be present in the crown compounds than those to be connected or bridged; protective groups can be used to shield these N atoms during the synthesis. The connecting chain or bridging group can be an alkylene radical, wherein, optionally, one or more chain C-atoms are replaced by hetero atoms such as O, N, or S or by an arylene group such as phenylene. The bridge in the clam compound can range from 1 to 20 atoms in length or it can be longer. A preferred class of clam compounds has a bridge which is derived from a polymer having a molecular weight up to about 5000. Numerous combinations for bridging chains will be apparent from this disclosure to those skilled in the art. The bridge can be a chain of carbon and hetero atoms such as defined by the bracketed portion of Formula I. Preferably no two hetero atoms in the bridge are adjacent and the total number of carbon and hetero atoms ranges from 1 to about 40. A preferred class of clam compounds has a carbon/hetero atom bridge which is substantially an alkylene bridge, i.e., the majority of the bridge atoms are carbon atoms.

The bridging process can be done by reacting an imino crown having a —NH-group with an appropriate difunctional reactant. Example 5 illustrates conversion of an imino crown to its Li salt with n-butyl Li and the reaction of that salt with an ω-alkylene diprimary dihalide to form a clam as a di-tertiary amine. Direct reaction of an imino crown with a diacyl halide, e.g. adipoyl chloride

forms a clam as a ditertiary amide; phosgene forms a claim as a urea (thiophosgene will give the thioureal. The bridge may be built in situ by reacting alkylene oxides, e.g. ethylene and propylene oxide, with an imino crown. Direct reaction of an imino crown with a diisocyanate gives a clam as a urea; typical diisocyanates are 1,6-hexamethylene diisocyanate, 2,4-toluenediisocyanate, and the reaction product of an excess of 2,4-toluenediisocyanate with poly(propyleneether) glycol.

The crown product can be isolated and recovered by conventional methods such as by concentration of the reaction mixture or by mechanical collection of insoluble (or precipitated) product. The crown compounds are freed from impurities, such as straight-chain reactants by recrystallization from organic liquids such as alcohol, chloroform, ethanol, benzene and heptane.

Carbocyclic nuclei or rings fused in the macrocyclic ring can be either aromatic or saturated. In general, complexes formed with saturated crown compounds are more soluble and stable in aliphatic solvents than are those formed with aromatic crown compounds. On the other hand, presence in the crown compound of aromatic nuclei carries with it certain advantages. For example, complex formation with aromatic crowns can be followed by commercial ultraviolet spectrophotometers. The fully saturated crown compounds do not absorb within the limits of such instruments. By appropriate choice of reactants or by partially hydrogenating aromatic crown compounds, so as to obtain compounds having both aromatic and saturated nuclei fused thereto, compounds having the advantages of each type can be prepared.

Various methods of incorporating saturated carbocyclic nuclei in the crown compounds will be apparent to those skilled in the art from this disclosure. For example, 1,2-diaminocyclohexane can be reacted directly with the dihalide reactant to produce a macrocyclic ring having cyclohexane fused to it. Again, saturated compounds like 1,2-bis($\beta$-chloroethoxy)cyclohexane can be reacted with an amino di-terminated open chain reactant to yield a saturated imine crown.

Aromatic crowns can be fully or partially saturated by catalytic hydrogenation. The temperature of hydrogenation is suitably from 60° to 120° C. Pressures can range from 500 to 2000 psig. Typical times required are from 3 to 20 hours. It will be realized, however, that these values are not critical. Some cleavage of the macrocyclic ring occurs, leading to the formation of by-products in addition to the desired hydrogenation product. These products can be separated and the desired hydrogenation product can be isolated by conventional physical methods, such as fractional crystallization and the like from solvents such as alcohol, chloroform, 2-ethoxy-ethanol benzene and heptane, or by chromatographic separation. If the desired product does not otherwise contain active hydrogen groups, the reaction product can be reacted with reagents such as organic isocyanates, which react readily with hydroxy compounds, to facilitate separation of the products.

The crown compounds described herein can be used to form a novel complex with a compatible cation of a metal compound. Particularly noteworthy are the complexes formed with ionic alkali metal compounds and alkaline earth metal compounds. The cation can be inorganic or organic.

The complex forming ability of crown compounds generally depends upon ring size and the number of nitrogen and oxygen atoms in the compound. Complexing ability cannot be predicted with certainty prior to actually testing the cation or cations with various crown compounds. However, certain trends are noticeable. One is that the complexing ability for a series of crown compounds of a given ring size is less for the alkali and alkaline earth metal cations for the compounds having fewer oxygen atoms in the ring. The complex forming ability for a series of crown compounds of a given ring size is greater for $Ag^+$ with those compounds having more nitrogen atoms in the ring. lantern compounds exhibit considerably stronger complexing ability for appropriate cations than monocyclic ring crowns of comparable ring size.

The complexes appear to be electrostatic in character rather than coordination complexes for alkali and alkaline earth cations. A complex can be formed with a cation selected from a group of cations having various valences and sizes. In most crown complexes it is believed that the cation is located near the center of the macrocyclic ring. A complex can have more than one ring per cation especially with large cations. Under some circumstances the complex can be solvated. The crown compounds of this invention can form complexes with the cations $Na^+$, $K^+$, $Ag^+$, $Ba^{++}$, $Sr^{++}$, $Ca^{++}$, $Rb^+$ and probably others. Other cations, such as $Li^+$, $Cs^+$, $Cu^+$, $Au^+$, $NH_4^+$, $RNH_3^+$, $Hg^+$, $Hg^{++}$, $Tl^+$, $Pb^{++}$, $Ce^{+++}$ and the like form complexes with similar crown compounds.

In complexes of alkali metal compounds and the like, substituents on the macrocyclic imine ring as described herein do not greatly affect the formation of the crown complexes. However, substituents do influence considerably some other properties of the complexes, particularly the solubility. In general the saturated crown compounds form complexes which are more soluble in most common solvents than complexes formed with the corresponding aromatic compound. In some instances, the complexes and more soluble in organic solvents than the crown compounds themselves.

Imine groups and substitutents on the macrocyclic ring affect the ability to convert the crown compound and complex to other compounds and the ability to atach other compounds to the crown compound and complex.

Complexes of the macrocyclic imines with compounds of alkali metals or alkaline earth metals can be prepared by a variety of methods. Crystalline complexes can be prepared by dissolving the crown compound and a cation source in a suitable solvent which is later removed by evaporation from the resulting complex, usually under vacuum. Alternatively, complexes can be prepared by dissolving crown compound and metal compound in a minimum quantity of hot solvent which dissolves each, the resulting complex being precipitated by cooling and mechanically separated, e.g., by filtration, centrifugation, etc. Again, crown compound can be heated with metal compound in a solvent in which only the latter is readily soluble, the crown compound being converted into a crystalline complex without the system even becoming a clear solution. The complex is then recovered by filtration. Other methods of complex formation will occur to the art-skilled in light of the above.

In general, selected complexes prepared according to this invention can solubilize complexed metal compounds in media wherein the are normally insoluble. This property alone suggests manifold applications of the invention in industry. For example, the benzene-soluble potassium hydroxide complex can be employed to initiate the anionic polymerization of acrylonitrile or pivalolactone, a hydroxylterminated polymer product resulting. It can also be used as a soluble acid-acceptor in nonprotic systems.

The crown compounds are useful for the separation of dissolved salts. The salt which can form a crown complex can thereafter be extracted by an immiscible solvent which cannot dissolve the uncomplexed salts present. By way of illustration, water-soluble salts that form crowned complexes can be separated from salts that do not; a water-insoluble solvent for the complex is employed for the extraction. For example, 2,3-(4'-methylbenzo-1,4-diamino-7,10,13,16-tetraoxacyclooctadeca-2-ene does not complex with magnesium ion; hence, silver salts can be separated from magnesium salts by this method.

The crown compounds of the invention can also be used as dye intermediates by adding an active hydrogen-containing substituent, e.g. OH—, amino, etc. to the aromatic nucleus by conventional techniques and thereafter coupling the compound with a diazo compound according to well-known methods.

The following examples are illustrative of compounds of the invention. Parts, proportions, and percentages are by weight unless otherwise stated.

EXAMPLE I

A. Preparation of 2,3-benzo-1-aza-4,7,10,13-tetraoxacyclopentadeca-2-ene or "1-aza-2,3-benzo-15 crown-5"

which has the following formula is accomplished as follows:

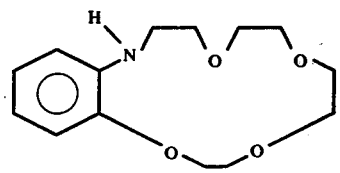

o-Aminophenol (17.1 grams, 0.157 gram-mol), 1,11-dichloro-3,6,9-trioxaundecane (36.6 grams, 0.157 gram-mol), and 250 milliliters of n-butanol at 25° C. are added to a one-liter, round-bottom glass flask equipped with a thermometer, a water-cooled reflux condensor, and an agitator and continually maintained under a protective nitrogen atmosphere. After the resulting mixture has been refluxed, while agitated, at a pot temperature of 121° C. for 18 hours, it is cooled to 67° C. A solution of 12.6 grams (0.315 gram mol) of sodium hydroxide in 12 milliliters of water is added. Then the resulting mixture is refluxed, while agitated, at a pot temperature of 101° C. for 10 hours.

The crown compound is isolated as follows:

The warm reaction mass obtained above is filtered and the filtrate is freed from volatiles by heating in a steam heated rotary vacuum evaporator at 100° C. and 0.2 mm. Hg. The residue, about 42 grams of brown viscous oil, is dissolved in 200 ml. of chloroform. The solution is twice washed with 100 ml. of 5% aqueous sodium hydroxide; it is dried over 20 grams of anhydrous magnesium sulfate, filtered, and concentrated in a rotary vacuum evaporator at 100° C. and 0.2 mm. Hg. The residue, 35.2 grams of brown viscous oil, is distilled in a steam heated rotary vacuum evaporator at 100° C. and 0.2 mm. Hg. The distillate, about 10.3 grams of liquid, is solidified into white crystals which is 2,3-benzo-1-aza-4,7,10,13-tetraoxacyclopentadeca-2-ene or "1-aza-2,3-benzo-15 crown-5". Recrystallization of the crown compound from n-heptane produces shiny white crystals melting at 100°–101° C.

Infrared spectra (IR) show a sharp infrared band at 2.98 microns besides the broad ether bands. The nuclear magnetic resonance (NMR) spectrum is consisten with the indicated structure. NMR is a standard method of structure determination. It is described in detail in *Application of Nuclear Mangetic Resonance Spectroscopy in Organic Chemistry* by Jackman and Sternhill, Pergamon Press New York, 2nd ed., 1969, and *Nuclear Magnetic Resonance Application to Organic Chemistry* by Roberts, McGraw-Hill Book Company, New York, 1959. Analysis yields the following data:

| Analysis: | Analytical | Calculated for $C_{14}H_{21}NO_4$ |
|---|---|---|
| C:% | 62.5, 62.7 | 62.9 |
| H:% | 7.9, 7.9 | 7.9 |
| N:% | 5.1 | 5.2 |
| Mol. Wt. | 272 | 267 |

B. Preparation of N-nitroso derivative of 2,3-Benzo-1-aza-4,7,10,13-tetraoxacyclopentadeca-2-ene is accomplished as follows. 2,3-Benzo-1-aza-4,7,10,13-tetraoxacyclopentadeca-2-ene (3.2 grams, 0.012 gram-mol), sodium nitrite (0.825 gram, 0.012 gram-mol), 5 ml. of concentrated hydrochloric acid, and 100 grams of ice are mixed together and allowed to stand for 15 minutes. The excess sodium nitrite is destroyed with sodium sulfamide; the organic phase is extracted with two 150-ml portions of diethyl ether. The resulting ethereal solution is dried over magnesium sulfate and concentrated in a heated rotary vacuum evaporator at 40° C. and 0.2 mm. Hg. The residue (2.5 grams) is the desired N-nitroso derivative of 2,3-benzo-1-aza-4,7,10,13-tetraoxacyclopentadeca-2-ene. Recrystallization from n-heptane over Darco activated carbon from Atlas Powder Company produces white fiber (m.p. 95°–96° C.) crystals with the following analysis:

| Analysis: | Analytical | Calc'd for $C_{14}H_{20}N_2O_5$ |
|---|---|---|
| C:% | 56.8, 56.9 | 56.7 |
| H:% | 6.6, 6.7 | 6.8 |
| N:% | 9.4 | 9.5 |

C. Preparation of 2,3-(3'-Nitrosobenzo)-1-aza-4,7,10,13-tetraoxacyclopentadeca-2-ene is accomplished as follows One gram of N-nitroso derivative of 2,3-benzo-1-aza-4,7,10,13-tetraoxacyclopentadeca-2-ene is isomerized to the 3'-nitroso derivative by treatment with 10 ml. of cold concentrated hydrochloric acid. The resulting purplebrown solution is neutralized with concentrated aqueous ammonium hydroxide. The crown compound is taken up in diethyl ether and is obtained after the resulting solution has been dried over anhydrous magnesium sulfate. It is concentrated in a rotary evaporator under vacuum. The desired 3'-nitrosobenzo crown is a yellow-green solid (0.5 gram) with the following analysis:

| Analysis: | Analytical | Calc'd for $C_{14}H_{20}N_2O_5$ |
|---|---|---|
| %C | 59.1, 59.4 | 56.7 |
| %H | 7.0, 7.2 | 6.8 |
| %N | 7.3 | 9.5 |

EXAMPLE 2

Preparation of
2,3-Benzo-1-aza-4,7,10,13,16-pentaoxacyclooctadeca-2-ene represented by the following formula is accomplished according to the following procedure:

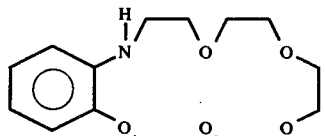

o-Aminophenol (20.7 grams, 0.19 gram-mol), 1,14-dichloro-3,6,8,12-tetraoxatetradecane (52.2 grams, 0.19 gram-mol), and 250 ml. of n-butanol at 25° C. are charged into the reactor and refluxed therein under nitrogen with good agitation for seven hours at a pot temperature of 121° C. Cooling is then applied to lower the temperature to 70° C. A solution of 15.3 grams (0.383 gram-mol) of sodium hydroxide in 16 ml. of water is added and the resulting mixture is refluxed for 15 hours at a pot temperature of 105°–101° C.

The warm reaction mixture is filtered. The filtrate is freed from volatiles by heating in a steam heated rotary evaporator at 100° C. and about 0.2 mm. Hg. The residue, 60.9 grams of viscous dark brown oil, is extracted with 400 ml. of n-heptane. Concentration of the heptane solution gives 12.6 grams of an orange liquid which is distilled in a steam heated rotary vacuum evaporator at 0.2 mm. Hg. The distillate, 9.3 grams of pale yellow oil, is the desired 2,3-benzo-1-aza-4,7,10-13,16-pentaoxacyclooctadeca-2-ene, which upon purification yields the following analysis:

| Analysis | Analytical | Calc'd for $C_{16}H_{25}NO_5$ |
|---|---|---|
| C:% | 59.5, 59.6 | 61.8 |
| H:% | 8.0, 8.0 | 8.0 |
| N:% | 3.9 | 4.5 |
| Molecular Wt. | 311 | 311 |

EXAMPLE 3

A. Preparation of
5,6,14,15-Dibenzo-4,7,10,13,16-pentaoxa-1-azacyclooctadeca-5,14-diene represented by the following formula is accomplished by the following procedure:

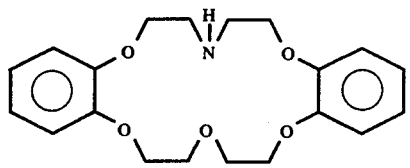

A 3-liter round-bottom glass flask, equipped with a stirrer, condenser, and addition funnel, is charged with 78 grams (0.027 gram-mol) of bis[2-(o-hydroxyphenoxy)ethyl]ether, 1700 ml. of n-butanol, and a solution of 33.0 grams (0.84 gram-mol) of sodium hydroxide in 100 ml. of water. The agitated mixture is heated to reflux; 50 grams (0.27 gram-mol) of 2,2'-dichloro-diethylamine hydrochloride are added. The resulting mixture is refluxed for two days, then cooled and filtered. Concentration by vacuum distillation of the filtrate yields a solid residue which is dissolved in hot benzene and filtered. Evaporation of the benzene gives 5,6,14,15-dibenzo-4,7,10,13,16-pentaoxa-1-azacycloocta deca-5,14-diene. Recrystallization from dioxane gives a 22% theoretical yield. A sample of this product, after recrystallization from toluene, melts at 152°–153° C. and has the following analysis which indicates the above formula:

| Analysis | Analytical | Calc'd for $C_{22}H_{29}NO_5$ |
|---|---|---|
| C:% | 66.9 | 66.85 |
| H:% | 6.9 | 6.96 |
| N:% | 4.1 | 3.90 |

Its NMR spectrum is consistent with the above formula.

B. Preparation of N-Ethyl Derivative of 5,6,14,15-Dibenzo-4,7,10,13,16-pentaoxa-1-azacycloocta-5,14-diene is accomplished by the following procedure.

A 30-cc. stainless steel cylinder is charged with one gram (0.003 gram-mol) of 5,6,14,15-dibenzo-4,7,10,13,16-pentaoxa-1-azacyclooctadeca-5,14-diene, 15 ml. of benzene, 0.24 ml. of ethyl iodide, and 1.5 ml. (0.003 gram-mol) of 2N aqueous sodium hydroxide. The cylinder is then sealed, kept at 100° C. for 16 hours, cooled, and opened. The benzene layer inside the cylinder is separated from the aqueous caustic layer, boiled in the presence of a gram or so of Darco decolorizing charcoal, and filtered hot. White crystals of the N-ethyl derivative of the crown compound precipitate having a melting point of 130°–132° C. and the following analysis:

| Analysis: | Analytical | Calc'd for $C_{22}H_{29}NO_5$ |
|---|---|---|
| C:% | 68.2, 67.7 | 68.2 |
| H:% | 7.5, 7.8 | 7.5 |
| N:% | 3.6, 3.7 | 3.6 |

C. Preparation of N-octyl Derivative of 5,6,14,15-Dibenzo-4,7,10,13,16-pentaoxa-1-azacyclooctadeca-5,14-diene is accomplished by the following procedure.

An oven dried, 500-ml. round-bottom glass flask equipped with a dry condenser, addition funnel, and stirrer is charged, successively, with 6.3 ml. (0.01 gram-mol) of a 15% solution of n-butyl lithium in hexane (commercially available from Foote Chemical), 20 ml. of the dimethyl ether of diethylene glycol, and a solution of 3.6 grams (0.01 gram-mol) of 5,6,14,15-dibenzo-4,7,10,13,16-pentaoxa-1-azacyclooctadeca-5,14-diene in the dimethyl ether of diethylene glycol. This mixture is heated to 110° C. and kept at 110° C. for 2 hours; a solution of 2 grams (0.01 gram-mol) of n-octyl bromide 150 ml. of anhydrous dimethyl ether of diethylene glycol is slowly added. The resulting mixture is then refluxed for 16 hours. On cooling, solids precipitate. These are removed by filtration after addition of 20 ml. of methanol. The filtrate is evaporated to dryness yielding the crude N-octyl derivative. This product is eluted from a neutral Woelm alumina column with benzene to produce several fractions which are combined and concentrated. Recrystallization of the resulting residue from ethanol gives 1.6 grams (34% theoretical yield) of the N-octyl derivative of 5,6,14,15-dibenzo-4,7,10,13-16-pentaoxa-1-azacyclooctadeca-5,14-diene. This product melts at 109°–110° C. and has the following analysis:

| Analysis: | Analytical | Cal'd for $C_{28}H_{41}NO_5$ |
|---|---|---|
| C:% | 71.5, 71.8 | 71.3 |
| H:% | 8.6, 8.7 | 8.6 |
| N:% | 2.9, 2.9 | 2.9 |

Nuclear magnetic resonance (NMR) analysis yields the following values which are consistent with the structure shown:
tau (3.1, s), tau (5.85, m) tau(6.75, t), tau(7.35, t), tau(8.65,s)

D. N-Acetyl Derivative of 5,6,14,15-Dibenzo-4,7,10,13,16-pentaoxa-1-azacyclooctadeca-5,14-diene is prepared according to the following procedure.

A 250-ml. round-bottom glass flask equipped with an agitator, thermometer, and condenser is charged with 100 ml. of toluene, one gram (0.002 gram-mol) of 5,6,14,15-dibenzo-4,7,10,13,16-pentaoxa-1-azacyclotadecea-5,14-diene, 0.2 ml. (0.004 gram-mol) of pyridine, and 0.2 ml. (0.004 gram-mol) of acetyl chloride. The mixture is refluxed for 1.5 hours, then cooled and diluted with 50 ml. of water. The organic and aqueous layers are separated, and the organic layer concentrated to give the N-acetyl derivative of 5,6,14,15-dibenzy-4,7,10,13,16-pentaoxa-1-azacyclooctadeca-5,14-diene. After this product has been recrystallized from benzene, it produces white crystals having a melting point of 198° C. and the following analysis:

| Analysis: | Analytical | Calc'd. for $C_{22}H_{27}NO_6$ |
|---|---|---|
| C:% | 66.1 | 65.8 |
| H:% | 7.1 | 6.7 |
| N:% | 3.4 | 3.5 |

NMR: consistent with structure.

EXAMPLE 4

A. Preparation of o-Bis[2-(p-toluenesulfonyl)ethoxy]benzene is accomplished by the following procedure A 2-liter round-bottom glass flask equipped with a stirrer, condenser, and thermometer is charged with 104 ml. (1.3 gram-mol) of pyridine and 32.6 grams (0.16 gram-mol) of o-bis[2-(hydroxy)ethoxy] benzene, the O,O'-bis [2-hydroxyethyl] derivative of catechol. This agitated mixture is cooled to 0° C. and grams 68 grams (0.35 gram-mol) of p-toluene sulfonyl chloride are added at such a rate that the temperature does not exceed 15° C. Agitation is continued for 3 more hours. A chilled solution of 210 ml. of concentrated hydrochloric acid in 470 ml. of water is added dropwise to the flask. Solid ditosylate, o-bis [2-p-toluenesulfonyl)ethoxy] benzene is filtered off and air dried. It melts at 95°–96° C. NMR is consistent with structure.

B. Preparation of o-Bis[2-(N-benzylamino)ethoxy]benzene is accomplished by the following procedure A 10.7 gram (0.10 gram-mol) portion of benzylamine is added to a solution of 5 grams (0.01 gram-mol) of the ditosylate prepared according to the above procedure in 100 ml. of xylene. The resulting mixture is agitated at reflux for 16 hours; it is cooled to precipitate as undesired white fibrous by-product which is filtered off. Concentration of the filtrate under vacuum gives nearly pure o-bis[2-(N-benzylamino)ethoxy] benzene. The diamine can be used without further purification.

C. Preparation of the N,N'-Dibenzyl Derivative of 5,6,14,15-Dibenzo-4,7,13,16-tetraoxa-1,10-diazacyclooctadeca-5,14-diene represented by the following formula is accomplished by the following procedure:

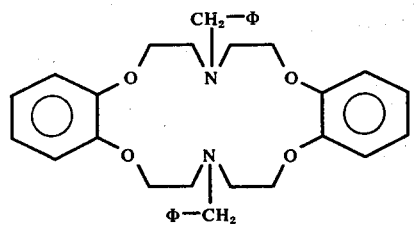

An 8-gram (0.02 gram-mol) sample of the diamine, prepared according to the above procedure, 200 ml. of xylene, 10.2 grams (0.02 gram-mol) of o-bis[2-(p-toluenesulfonyl)ethoxy]benzene, and 5.7 grams (0.04 gram-mol) of tri-n-propylamine are agitated at reflux for 16 hours in a 500-cc. round-bottom glass flask. The reaction mixture is subsequently cooled; the solution is decanted from a tarry residue and concentrated by evaporation of the xylene to yield crude product. Boiling methanol is used to extract the impurities from it which leaves the undissolved N,N'-dibenzyl derivative of 5,6,14,15-dibenzo-4,7,13,16-tetraoxa-1,10-diazacyclooctadeca-5,14-diene, having a melting point of 176° C. and the following NMR spectrum which is consistent with the structure; nmr:tau(2.7,m), tau(3.2,s), tau(5.9,t), tau(6.2,s), tau(6.85,t). This compound is used without further purification.

D. Preparation of 5,6,14,15-Dibenzo-4,7,13,16-tetraoxa-1,10-diazacyclooctadeca-5,14-diene represented by the following formuls is accomplished by the following procedure:

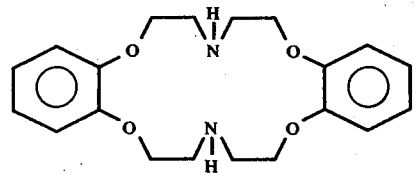

A 4-gram sample of N,N'-dibenzyl derivative of 5,6,14,15-dibenzo-4,7,13,16-tetraoxa-1,10-diazacyclooctadeca-5,14-diene prepared as above is dissolved in 300 ml. of tetrahydrofuran. One gram of palladium-on-charcoal catalyst is added; the mixture is hydrogenated at 50° C. and 100 psig. for 6 hours. Solids are removed from the hydrogenation mixture by filtration; the tetrahydrofuran is evaporated. The crude residue is purified by refluxing with methanol to dissolve the crown compound. The product is obtained by evaporating the methanol and recrystallizing from toluene to give 2.1 grams (80% theoretical yield) of 5,6,14,15-dibenzo-4,7,13,16-tetraoxa-1,10-diazacyclooctadeca-5,14-diene as white crystals melting at 175°–176° C. and having the following analysis:

| Analysis: | Analytical | Calc'd for $C_{20}H_{26}N_2O_4$ |
|---|---|---|
| C:% | 66.8 | 67.0 |
| H:% | 7.4 | 7.3 |
| N:% | 7.8 | 7.8 | nmr: tau(3.15,s), tau(5.9,t), tau(6.9,t), tau(7.55,s)

The product is evaluated for ion complexing properties by forming a solution of a salt such as potassium chloride or silver nitrate. The potassium salt is conveniently ionized in methanol and the silver salt is conveniently ionized in water. Under ambient conditions, solutions of 5,6,14,15-Dibenzo-4,7,13,16-tetraoxa-1,10-diazacyclooctadeca-5,14-diene, in the same solvent as the salt, are added to the salt solutions. Complexes with the metal ions form upon addition of the crown compounds. The degree of complex formation is determined by potentiometric measurement of the salt solutions before and after the additions of crown compounds, using the apparatus and calculation methods described in detail in Frensdorff Journal of the American Chemical Society 93,600 (1971) "Stability Constants of Cyclic Polyether Complexes with Univalent Cations." The silver complex of the crown compound of the present example is found to exhibit an equilibrium constant in water of about $10^7$ liters/mole. This is significantly higher than the equilibrium constant of about $10^2$ liters/mole found for silver complexes of similar crown compounds without nitrogen ring components. The potassium complex of the present crown compound exhibits an equilibrium constant of about $10^{1.6}$ liters/mole in methanol, while the equilibrium constant of potassium complexes of similar crown compounds without nitrogen ring components is about $10^5$ liters/mole. Magnesium ion complexes much less readily than silver with the crown compounds, similarly permitting separation of a mixture of such ions.

The metal complexes of the crown compound can be isolated by evaporation or by crystallization from a concentrated solution. The crown complexes can then be separated from undesirable salts by dissolving the crown complex in an organic solvent such as chloroform, in which an inorganic salt would not be soluble.

EXAMPLE 5

Preparation of N,N'-Decamethylenebis[5,6,14,15-dibenzo-4,7,10,13,16-pentaoxa-1-azacyclooctadeca-5,14-diene]

represented by the following formula is accomplished by the following procedure:

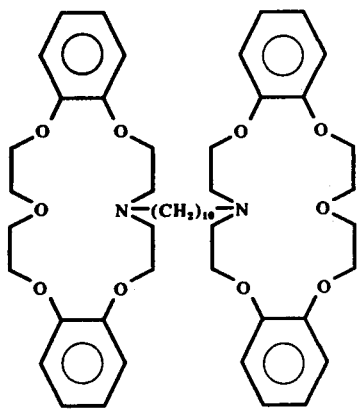

A dry 250-ml. round-bottom 3-neck glass flask equipped with a stirrer, condenser, and addition funnel, is charged under nitrogen with 100 ml. of anhydrous dimethyl ether of diethylene glycol and 1.8 grams (0.005 gram-mol) of 5,6,14,15-dibenzo-4,7,10,13,16-pentaoxa-1-azacyclooctadeca-5,14-diene. The mixture is heated and when the crown compound has dissolved, 3 ml. (0.005 gram-mol) of a 15% solution of n-butyl lithium in hexane is added. After the resulting mixture begins to reflux, a solution of 0.75 gram (0.0025 gram-mol) of 1,10-dibromodecane in 10 ml. of the dimethyl ether of diethyl glycol is added dropwise. The reaction mixture is refluxed and agitated for 16 hours.

The reactor is then cooled to room temperature. Twenty-five milliliters of methanol are introduced to use up any unreacted n-butyl lithium; the mixture is filtered; evaporation of solvents from the filtrate gives a residue which is dissolved in chloroform, filtered, and concentrated. The residue is dissolved in chloroform and chromatographed on a basic Woelm column. The chloroform fractions contain crystals which melt at 122°–124° C. after recrystallization. Recrystallization from toluene produces crystals which exhibit nmr spectra consistent with the expected structure of the clam compound N,N'-decamethylenebis[5,14,15-dibenzo-4,7,10,13,16-pentaoxa-1-azacyclooctadeca-5,14-diene] and having the following analysis:

| Analysis: | Analytical | Calc'd for $C_{50}H_{68}O_{10}N_2$ |
|---|---|---|
| C:% | 70.5 | 70.09 |
| H:% | 7.9 | 7.95 |
| N:% | 3.26 | 3.27 |

A 0.0001 molar solution of the clam compound is prepared in ethanol. The metal ions $Na^+$ and $Cs^+$ are added to the clam-ethanol solutions as salts. Ultraviolet spectra of these solutions indicate that a small amount of the $Na^+$ is complexed by the clam compound but none of the $Cs^+$.

EXAMPLE 6 -Lantern Compound

Preparation of 5,6,14,15,22,23-Tribenzo-4,7,13,16,21,24-hexaoxa-1,10-diaza-bicyclo[8.8.8]-hexacosa-5,14,22-triene represented by the following formula is accomplished by the following procedure.

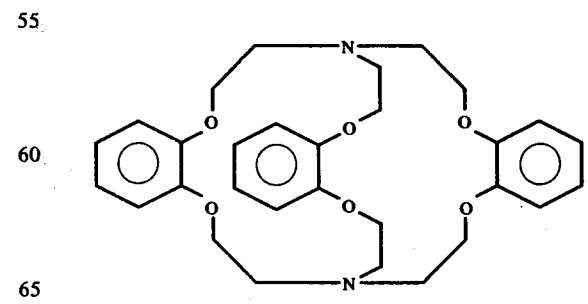

A dry 2-liter round-bottom glass flask, equipped with a stirrer, condenser, and addition funnel, is charged with 3.58 grams (0.01 gram-mol) of crown compound 5,6,14,15-dibenzo-4,7,13,16-tetraoxa-1,10-diazacyclooctadeca-5,14-diene (prepared according to the procedure of Part D of Example 4) and one liter of the anhydrous dimethyl ether of diethylene glycol under a nitrogen blanket. The mixture is heated until the crown compound dissolves. Then 12.5 ml. of a 15% solution of n-butyl lithium in hexane are added. The mixture is heated to reflux and 5.1 grams (0.01 gram-mol) of the ditosylate of bis-[2-o(-hydroxyphenoxy)ethyl]ether are slowly introduced from the addition funnel. Refluxing is continued for two days.

After the mixture has been cooled, a 5 ml. aliquot of methanol is added. The resulting composition is filtered and the filtrate concentrated in a rotary vacuum evaporator. The brown viscous material which remains is added to about 30 ml. of chloroform. The resulting solution is extracted with water, dried, and concentrated to yield another viscous liquid. This residue is chromatographed on a basic Woelm alumina column (75 ml. capacity) using chloroform as solvent. The first two fractions eluted contain a small amount of starting material and other components. These fractions are combined and rechromatographed on another basic Woelm column, eluting with benzene. The yellow oil obtained on concentrating the eluates is boiled in about 400 ml. of hexane. The resulting hexane solution is decanted and concentrated to a 50-ml. volume; white crystals of the lantern compound precipitate and are collected by filtration. The lantern compound melts at 108°–113° C. and exhibits an nmr spectrum consistent with the proposed structure and has the following analysis.

| Analysis: | Analytical | Calc'd for $C_{36}H_{36}O_6N_2$ |
|---|---|---|
| C:% | 68.9 | 69.2 |
| H:% | 6.9 | 6.9 |
| N:% | 5.3 | 5.4 |

The products of Example 6 are tested for ion complexing ability in the manner described in Example 4D above. Using a potassium chloride salt in methanol the complex constant of the present lantern compound with potassium ion is about $10^{7 \, 0.3}$. This particularly high complexing ability makes the present compound especially useful in effecting reactions with potassium in media in which potassium would not be readily soluble.

We claim:
1. A macrocyclic compound of the formula

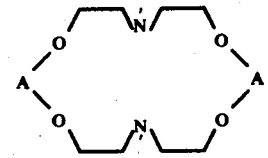

where A is a carbocyclic ring which is vicinally fused to the macrocyclic ring and is selected from the group consisting of (a) phenylene, naphthalene, phenanthralene, and anthralene, (b) the saturated analogs of (a), and the halo, nitro, nitroso, $-NH_2$, $C_1-C_4$ alkyl, $C_2-C_4$ alkenyl, $C_6-C_{12}$ aryl, $C_7-C_{16}$ aralkyl, $C_1-C_4$ alkoxy, cyano, hydroxy, carboxy or sulfo derivatives thereof, and the third valence of the nitrogen atoms is occupied with a member of selected from the group consisting of hydrogen,

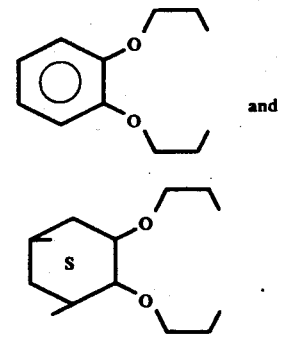

and

2. The macrocyclic compound of claim 1 in which (a) is orthophenylene and the third valence of the nitrogen atom is occupied with

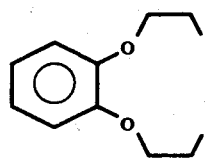

* * * * *